United States Patent [19]
Schneider et al.

[11] Patent Number: 5,414,014
[45] Date of Patent: May 9, 1995

[54] METHODS FOR EFFICACIOUS REMOVAL OF ATTACHED, SUCKING ANTROPODS FROM HUMAN DERMIS

[75] Inventors: Linda H. Schneider; Randall B. Murphy, both of Irvington, N.Y.

[73] Assignee: Innova Biomed, Inc., Irvington, N.J.

[21] Appl. No.: 46,195

[22] Filed: Apr. 8, 1993

[51] Int. Cl.$^6$ .................. A61K 31/24; A61K 37/14; A61K 31/70; A61K 31/56
[52] U.S. Cl. ........................... 514/535; 514/6; 514/31; 514/179; 514/530; 514/536; 514/724; 514/946; 514/947
[58] Field of Search ............... 514/535, 536, 946, 947, 514/6, 31, 179, 530, 724

[56] References Cited
U.S. PATENT DOCUMENTS

| | | | |
|---|---|---|---|
| 4,091,090 | 5/1978 | Sipos | 514/944 |
| 4,960,771 | 10/1990 | Rajadhyaksha | 514/947 |

*Primary Examiner*—Raymond Henley, III
*Assistant Examiner*—K. Weddington
*Attorney, Agent, or Firm*—Omri M. Behr; Matthew J. McDonald

[57] ABSTRACT

The present invention provides methods of using compositions containing local anesthetic compounds for facilitating the removal of sucking arthropods from the skin of a mammal; for reducing inflammation associated with a bite of a sucking arthropod; for limiting infection from a sucking arthropod; and for enhancing the facilitated removal of sucking arthropods from the skin of a mammal.

5 Claims, No Drawings

METHODS FOR EFFICACIOUS REMOVAL OF ATTACHED, SUCKING ANTROPODS FROM HUMAN DERMIS

FIELD OF THE INVENTION

The present invention relates to a formulation and the use of compositions for removal of attached sucking arthropods, and methods for effecting removal of sucking arthropods. These arthropods include organisms commonly known as the "tick." The invention provides a novel composition and the following novel applications thereof: (a) facilitating removal of the entire body of said arthropods, including mouth or feeding parts, from the skin of an animal or Man; (b) enhancing said facilitated removal of such sucking arthropods; (c) reducing or ameliorating the inflammatory reaction and pain in human and animal dermis and endodermis (hereinafter "skin ") commonly associated with biting and attachment by such sucking arthropods; and (d) inclusion in a kit for removing said sucking arthropods.

BACKGROUND OF THE INVENTION

Numerous diseases of Man and animals are carried by sucking arthropods as a primary vector of infection. Causative agents of these diseases include viruses, bacteria and rickettsia, each of which is transferred to Man and animals by the arthropod's bite.

Diseases which may be transmitted to Man or animals by the tick include Lyme Disease (also known as Borreliosis, Lyme Borreliosis-associated Encephalopathy, Lyme Arthritis, acrodermatitis chronica atrophicans, erythremia chronicurn migrans, Banwarth's syndrome, tick-borne meningopolyneuritis, Lyme meningitis, collectively hereinafter termed "Lyme Disease"). The causative organism of Lyme Disease is the spirochete *Borrelia Burgdorferi*. Other tick-borne diseases include Rocky Mountain Spotted Fever (causative agent, *Rickettsia rickettsii*); Q fever (causative agent, *Rickettsia burnetii*); Tularemia (causative agent, *Pasteurella tularensis*); South African Tick Bite Fever (causative agent, *Rickettsia pijperi*); Mediterranean fever (causative agent, *Rickettsia conori*); Human Babeosis (causative agent, *Babesia Microti*); epidemic Typhus (causative agent, *Rickettsia prowazekii*); and Scrub Typhus (causative agent, *Rickettsia tsutsugamushi*). Even anaphylaxis has been caused by the attachment and bite of an arthropod (*Ixodus pacificus*). See, e.g. Boyd, A TEXTBOOK OF PATHOLOGY, Eighth Edition, Asian Edition, Lee and Febiger (1976), pp. 395–399 and pp. 71 6; Robbins, PATHOLOGY, third edition, W.B. Saunders, Philadelphia (1967), pp. 349–353.

The most ubiquitous of such sucking arthropods is commonly referred to as the tick, of which there are numerous species and subspecies. Ticks established to be disease vectors include *Ixodes dammini* (commonly termed the deer tick), *Ixodes scapularis, Amblyomma arnericanum, Amblyomma maculatum, Ixodes pacificus, Ixodes ricinus, Ixodes persulcatus, Ixodes hyocyclus, Dermacentor andersoni*. See Sigal and Curran, Ann. Rev. Publ. Health 12: 85–109 (1991); also Tetlow et al. Am. J. Trop. Medo Hygiene 44:469–474 (1991); See also Piesman et al., J. Clin. Microbiol. 25: 2012–2013 (1987).

("Disease Organism" refers to any of the viral, bacterial or rickettsial microbiological agents which are normally contained in the gut or vascular system of the infected tick, and which may be transmitted to Man or Animals during the sustained attachment of the tick to the dermis or subcutaneous tissues of such mammalian species. "Tick" refers to any of the species of arthropods which are named above as significant vectors for the infectious organisms in the disease of Man and Animals enumerated above.)

Lyme Disease is probably the most widespread and frequently encountered arthropod-borne disease. It is particularly problematic to treat because it is an essentially multisystem inflammatory disease with complex symptomatology often not unique to the disease. Consequently, considerable confusion has taken place in attempts to diagnose Lyme Disease due to the absence, until recently, of reliable immunological tests for the organism. Diagnosis has been even more challenging in those cases where an initial skin lesion does not appear in a reasonable time following the tick bite. Additionally, even when Lyme Disease is correctly diagnosed, there have been problems in treating it: despite antibiotic therapy, Lyme Disease sometimes presents chronic symptoms.

Therefore, efforts have been made to prevent Lyme Disease, and other tick-borne diseases, by eradicating tick populations from areas where Man and animal are likely to become infected. However, it is exceedingly difficult to rid an area of Lyme Disease-carrying vectors. One reason is that carrier ticks, generally of the family Ixodes, are usually present as a very highly concentrated population. Many animals in a given area themselves carry ticks harboring the Lyme Disease causative agent; non-domesticated animals infected with *B. Burgdorferi* generally include coyotes, deer, mice, jackrabbits, raccoons and hamsters, while domesticated animals which may be infected include cats, dogs, cows, horses, and sheep. Chemical means for clearing areas heavily infected with carrier ticks have failed to demonstrate significant reproducible lowering of Lyme Disease prevalence. Application of such agents not only has dubious effectiveness in reducing Lyme Disease morbidity; these agents may themselves have toxic impact on other wildlife and so render their use undesirable.

Lyme Disease is also preventable by removal of the sucking arthropod soon after its bite. This has generally not been an effective prophylactic measure to date because tick bites are often undetectable or ignored. Nevertheless, if tick removal occurs soon enough after the bite, the arthropod will not have had time to transfer disease organisms to the Man or animal host.

The importance of prompt tick removal is made clear by the correlation between the time a tick remains attached after biting its host and the number of infections caused by tick-borne organisms in a controlled population. This correlation is demonstrated by the data in TABLE 1, showing the time-course for which the tick must remain attached in order for demonstrated spirochetal infection to occur in the rabbit (adapted from the data of Piesman et al., supra).

TABLE 1

| Hours of Attachment | Number of Ticks/Rabbit | Infection Observed |
|---|---|---|
| 24 | 15 | NO |
| 36 | 19 | NO |
| 48 | 15 | NO |
| >120 | 16 | YES |

It is important to note that prophylaxis by removal of the tick depends upon the entire arthropod being removed from host flesh. If removal is not complete, then head, mouth or feeding parts may remain in the host flesh. These parts may and often do contain disease organisms and hence are still capable of transmitting disease-causing organisms for up to several days after removal of most of the tick. To be effective as a means of disease prophylaxis, removal of the entire tick is crucial. Complete removal also constitutes a diagnostic aid. Thus when the complete, untraumatized tick body is successfully removed from host flesh, the tick may readily be classified taxonomically or immuno-histochemically. Thus, one may determine whether the tick is one which may bear disease organisms.

It is exactly this completeness of removal which poses a major difficulty in prophylaxis of Lyme Disease and other arthropod-borne diseases. Due to its small size (0.3–2 mm in length), once the tick has bitten a host and the host's tissue surrounding the bite has swollen, the head and abdomen of the tick usually become wholly or partially surrounded or submerged in the host's epidermis. Therefore, only a small area of the tick may be gripped with a forceps or other removal tool. Further, the head and particularly the mouth parts also have an exceedingly retentive hold in the host skin. Thus, the parts most difficult to disengage cannot readily be grasped. Finally, when the exposed part of the tick is grasped during removal, the very tight hold by the mouth parts frequently causes breakage of the tick body, even when experienced medical personnel attempt removal of an arthropod.

Unfortunately, this important aspect of disease prophylaxis has received comparatively little attention, and incorrect methods of tick removal are abundant in both the professional literature and popular literature. Old wives' tales suggesting that kerosene, petroleum jelly, or a lit match or cigarette are effective in tick removal are simply unreliable. These methods should be eschewed, as they may actually cause the tick to regurgitate into the wound and cause infection. It is actually desirable for ticks to be removed with thin tweezers or forceps using antiseptic precautions.

Prior art compositions have employed refrigerant (U.S. Pat. No. 4,834,967) and gas anesthetic compounds (U.S. Pat. No. 4,534,128 and 4,624,070) for tick removal or control, respectively. U.S. Pat. No. 4,834,967 discloses ticks removal from the skin of a mammal by means of a liquid refrigerant applied to the skin to freeze, kill, and dislodge the tick. The liquid refrigerants disclosed include Freon R-12, Freon R-22, Freon R-502, liquid nitrogen, and liquid carbon dioxide. The refrigerant is said to kill the tick by freezing it. Although application of such refrigerants could cause temporary numbness to the dermis of the mammal to which it was applied, the refrigerant does not act as a local anesthetic. Furthermore, the tick is said to be killed by freezing; it appears no selective paralysis of the tick occurs.

U.S. Pat. Nos. 4,534,128 and 4,624,070 disclose use of a general anesthetic, dimethyl ether, for pest control. A method of immobilizing and killing insects in their dwelling place by applying mixtures of dimethyl ether and various insecticides (not repellents) in a directed spray, and an apparatus for said application, are described. While dimethyl ether gas is a general anesthetic, it is not used as an anesthetic due to its relatively toxic effect in animals and Man.

Given the difficulty of removing sucking arthropods from host skin coupled with the desirability of doing so to prevent Lyme Disease, there has been a long-felt need for compositions facilitating the simple, effective and a traumatic removal of attached sucking arthropods from human or animal skin. Such compositions should be safe for handling by laymen. These compositions should also effect complete removal of the tick; this would further allow subsequent characterization of the tick by taxonomical and/or immunological means. The compositions should also act rapidly to facilitate tick removal, prevent infection and reduce inflammation of tissue at or surrounding the bite, and enhance quick removal of ticks.

There has been an equally long felt need for methods which facilitate removal of attached sucking arthropods from human or animal skin.

(Citation of documents herein is not intended as an admission that any of the documents cited herein is pertinent prior art, or an admission that the cited documents is considered material to the patentability of the claims of the present application. All statements as to the date or representation as to the contents of these documents is based upon the information available to the applicant and does not constitute any admission as to the correctness of the dates or contents of these documents.)

SUMMARY OF THE INVENTION

The present invention provides compositions and methods for removal of attached sucking arthropods from human or animal skin, which involve topical application of local anesthetic chemical entities; methods of using the composition; as well as a kit for removal of sucking arthropods. It is believed the anesthetic entities paralyze the feeding mouthparts of the arthropod, and hence allow removal of these arthropods in a prompt and effective manner, optimally prior to the transmission of disease organisms from the arthropod to Man or animal.

In one embodiment of the invention, a composition for topical application including the anesthetic lidocaine—a chemical entity also known as 2-(Dimethylamino)-N-(2,6-dimethylphenyl)-acetamide-2-diethylamino-2',6'-acetoxylidide, or omega-diethylamino-2,6-dimethyl-acetanilide—or a similar anesthetic, produces a desirable effect of facilitating removal of sucking arthropods.

More particularly, this composition contains 0.05–10% weight/volume of a primary anesthetic having the formula

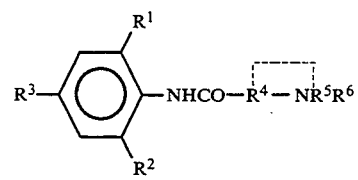

wherein
$R^1$=H, a $C_{1-4}$ alkyl or —COOCH$_3$;
$R^2$=H or a $C_{1-4}$ alkyl;
$R^3$=H or CH$_3$;
$R^4$=$C_{1-4}$ alkyl;
$R^5$ and $R^6$ independently=H or $C_{1-4}$ alkyl, where at least one of $R^1$ and $R^2$ is $C_{1-4}$ alkyl and where at least one of $R^5$ and $R^6$ is $C_{1-4}$ alkyl, provided that when $R^4$ and $R^5$ in

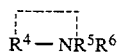

are joined, $R^4$ and $R^5$ together with N form a heterocycloalkyl moiety; or the hydrohalide thereof; and a water-soluble carrier which enhances skin permeability.

Preferably, in the primary anesthetic of Formula I, $R^1$ and $R^2=CH_3$; $R^3=H$; $R^4=CH_2$ or $CHCH_3$; $R^5=(CH_2)_nCH_3$ where $n=1-3$; and $R^6=H$ or $CH_2CH_3$. Preferred primary anesthetics include lidocaine, mesocaine, hostacaine, mepivacaine, bupivacaine and propiotocaine.

This embodiment further comprises at least one ingredient selected from the group consisting of i) a secondary anesthetic; ii) an anti-inflammatory compound; iii) an antibiotic, and iv) an insect repellant (suitably N,N'-diethyl-m-toluamide).

When present in the composition, the secondary anesthetic (at concentrations of from 0.05–20% weight/volume) serves to increase the anesthesia of host skin at the bite location. Suitable secondary anesthetic compounds include substituted esters of p-aminobenzoic acid having the formula:

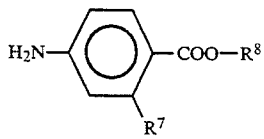

wherein $R^7=H$ or $Cl$; $R^8=C_{1-4}$ alkyl-X, where $X=H$ or $-\overset{\cdot}{N}(R^9)_2$, and $R^9=C_{1-4}$ alkyl, or the hydrohalide thereof.

Preferred secondary anesthetics include one or more of
benzocaine
chloroprocaine and
procaine,
or the hydrohalide of one or more of said secondary anesthetics.

When present in the composition, the anti-inflammatory compound (at concentrations of from 0.01 to 10% weight/volume) serves to lessen discomfort associated with arthropod bites such as reddening, swelling and itching. The anti-inflammatory compound may suitably be a topical astringent (exemplified by ethyl alcohol, thymolmethyl salicylate); an anti-inflammatory steroidal agent (exemplified by hydrocortisone); an antagonist of prostaglandin, inhibitor of prostaglandin synthetase or some other key prostaglandin enzyme; an antagonist of bradykinin selective for defined subtypes of bradykinin receptors; an inhibitor of histamine receptors selective for receptors of subtypes which are present in human or animal dermis, or in adjacent subcutaneous tissues; or an inhibitor of mast cell degranulation. Preferred anti-inflammatory compounds include steroids, prostaglandin antagonists and inhibitors of histamine receptors and/or of mast cell degranulation.

When present in the composition, the antibiotic serves to destroy tick-borne spirochetes and other disease organisms. Suitable antibiotics include but are not limited to bacitracin, polymyxin and nystatin.

When present in the composition, the insect repellent is present at concentrations of from 1 to 50% weight/volume.

Another embodiment of the invention is a method for facilitating removal of sucking arthropods from the skin of a mammal comprising topically applying a layer of the above-described composition one or more times to the sucking arthropod and immediately surrounding topical area, then waiting 5 to 30 minutes, or 10 to 20 minutes, before removing said sucking arthropod.

Because this method frequently allows rapid removal of arthropods with complete dislodgement of the feeding mouth parts, this method permits preservation of the complete arthropod, allowing it to be identified by skilled personnel. This not only greatly reduces the chances of infection from the arthropod, but permits determination as to whether the arthropod belongs to a disease-bearing group; and, if it does, allows diagnostic testing to identify those disease organisms carried by the arthropod, if any.

A further embodiment is a method of reducing inflammation associated with a sucking arthropod bite comprising topically applying the composition containing both a primary anesthetic and an anti-inflammatory compound to the sucking arthropod and the immediately surrounding topical area and making repeated topical application as desired.

Yet another embodiment of the invention is a method of limiting infection from a sucking arthropod comprising topically applying a thin layer of the composition containing both a primary anesthetic and an antibiotic one or more times to the sucking arthropod and the immediately surrounding area within 48 hours of receiving said bite; and making repeated topical applications of said composition to said area once every 5 to 30 or 10 to 20 minutes until said arthropod falls off or becomes easily removable. Optionally, one should then make up to 2 to 5 or 3 or 4 further applications after removal of said arthropod in order to kill any pathogenic microbes possibly regurgitated into the bite.

A further embodiment of the invention is a method of enhancing the facilitation of removing attached sucking arthropods by applying a composition containing both a primary anesthetic and an insect repellent topically to large areas of exposed skin, Yet a further embodiment of the invention is a method of using the composition described above to facilitate the removal of sucking arthropods from the skin of mammals, particularly humans and household pets which may serve as transmitters of ticks to the pet owners; or using the composition to limit infection from the arthropod; to reduce inflammation from arthropod bite; or to enhance the facilitation of removing arthropods soon after they bite.

In another embodiment, the invention provides a kit for removing sucking arthropods safely and quickly from the skin. The kit comprises a conveniently packaged amount of the above-described composition plus at least two supplemental items selected from the group consisting of a magnifying lens, a pair of forceps, a sterile alcohol wipe pad, a sterile bandage, and a container (vial) into which the removed tick is placed for subsequent analysis.

DETAILED DESCRIPTION OF THE PREFERRED EMBODIMENTS

In a first embodiment, the composition suitably includes 0.05–10% wt/vol. of a primary anesthetic having the formula

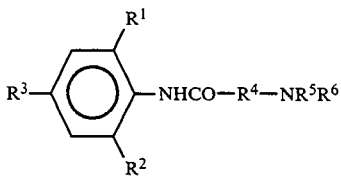

wherein $R^1$, $R^2$, $R^3$, $R^4$, $R^5$ and $R^6$ are defined as above, or the hydrohalide of one or more of said primary anesthetics; an ingredient selected from the group consisting of insect repellent, antibiotic, inflammatory agent and a secondary anesthetic which is a substituted ester p-aminobenzoic acid having the formula

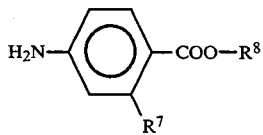

wherein $R^7$, $R^8$ (and $R^9$) are defined as above, or the hydrohalide of one or more of said secondary anesthetics; and a water soluble carrier which enhances skin permeability.

Primary Anesthetics

Although the number of chemical compounds with local anesthetizing activity is very high, only certain of these local anesthetics induce release of a sucking arthropod already attached to the dermis of an animal or Man. Thus, anesthetics structurally related to lidocaine selectively possess the ability to facilitate removal of a sucking arthropod, such as the deer tick *Ixodes dammini*, from its attachment to mammalian skin, while, unexpectedly, other local anesthetics (e.g., substituted esters of p-aminobenzoic acid, typified by benzocaine) do not aid release of a tick or other sucking arthropod from human or animal dermis.

Preferred primary anesthetic compounds are listed below followed by their generic name, their IUPAC name and their Merck Index number:

lidocaine—2-(Diethylamino)-N-(2,6-dimethylphenyl-)acetamide—5323
mesocaine—2-(Dimethylamino)-N-(2,4,6-trimethylphenyl)acetamide—9368 (also known as 2-diethylamino-2',4',6'-trimethylacetanilide)
hostacaine—2-(n-butylamino)-N-(2-methyl-6-chlorophenyl)acetamide—1498 (also known as 2-(butylamino)-N-(2-chloro-6-methylphenyl)acetamide)
mepivacaine—N-methylpiperidine-2-carboxylic acid-2,6-dimethylanilide—5688 (also known as N-(2,6-dimethylphenyl)-1-methyl-2-piperidinecarboxamide)
bupivacaine—1-butyl-2',6'-pipecolayxlidide—1480
baycaine—2-(Dimethylamino)-N-(2-methyl-6-carboxymethyl-phenyl)acetamide—9239 (also known as 2-(2-diethylaminoacetamido)-m-toluic acid methyl ester)
propiotocaine—2-(N-n-propylamino)-alanine-N-(o-toluamide)—7541 (also known as N-(2-methylphenyl)-2-(propylamino)-propanamide)

The primary anesthetics mepivacaine and bupivacaine each possess a chiral carbon, and therefore (R)- and (S)- enantiomers are known. These enantiomers have been resolved and were reported to differ in their length of action. Thus one of the shorter acting enantiomers may prove to be preferred in this composition.

In an especially preferred embodiment of the invention, the local anesthetic applied topically would be lidocaine in ointment form. This primary anesthetic may be used at concentrations ranging from 1.0% to 5.0% (w/v), preferably at 5.0%. As lidocaine is not well absorbed into Man or animals through intact skin, the application of substantial quantities of the ointment results in no significant toxic effects of any kind, as might conceivably result from the parenteral administration of an excessive quantity of the drug. Due to this poor absorption, the composition must include a carrier which enhances skin permeability, discussed below.

Skin Permeability Enhancing Carrier

Several of the primary anesthetic compounds including lidocaine have little ability to permeate through human skin. This low permeation level is not increased when the carrier for the composition is one which itself does not enhance skin permeability, e.g., petroleum jelly. When the primary anesthetic and its carrier have poor skin permeability, there is little permeation or seepage of this primary anesthetic from the host's skin surface to the arthropod's mouth parts. Consequently, the arthropod's mouth parts are only slightly loosened or not loosened at all, with the result that removal of the arthropod is delayed or not accomplished.

Therefore, a preferred embodiment of the composition has a carrier which enhances skin permeability. Suitable ingredients for this carrier are methyl paraben, propyl paraben, polyethylene glycol, polypropylene glycol, glycerol, propylene glycol, and ethyl alcohol. These ingredients as well as others which are known in the art may be used in widely varying relative amounts known to formulators of conventional topical applications, for example at from 0.05 to 15% weight/volume.

An especially preferred composition comprises 1–10% weight/volume of lidocaine and a water-soluble ointment or lotion carrier comprising 0.05–0.5% methylparaben, 0.05–0.5% propylparben, 1–10% polyethylene glycol 2000, and 5–25% polyethylene glycol 400, 15% ethyl alcohol (wt/vol) and up to 70% esters of mixed saturated fatty acids.

Secondary Anesthetic

The secondary anesthetic of the composition may suitably be any compound known to have physiological activity as a local anesthetic, as demonstrated by its actions in Man, animals, or other usual and conventional bioassay systems, but does not have the ability to induce release of the tick. Examples of this latter class of compounds include benzocaine, procaine or chloroprocaine, which do not appear to be effective in removing arthropods.

Suitable secondary anesthetic compounds include substituted esters of p-aminobenzoic acid having the formula:

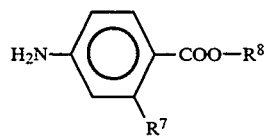

wherein $R^7$=H or Cl; $R^8$=$C_{1-4}$alkyl-X, where X=H or —$N(R^9)_2$, and $R^9$=$C_{1-4}$ alkyl, or the hydrohalide thereof. These compounds may be present at 0.05–10% wt/vol of the composition.

Preferred secondary anesthetics are identified below by their generic name, their IUPAC names and their Merck Index number:
benzocaine—ethyl aminobenzoate—3691
chloroprocaine—4-amino-2-chlorobenzoic acid 2-diethylaminoethyl ester—2140
procaine—4-aminobenzoic acid 2-(di-ethylamino)ethyl ester—7554 or the hydrohalide of one or more of said secondary anesthetics.

Anti-Inflammatory Agent

The composition may further contain, as a secondary active, agents which reduce or minimize the phenomena of inflammatory reactions, (e.g., swelling, itching and reddening of the skin around an arthropod bite). These agents are exemplified but not limited to topical astringents (exemplified by ethyl alcohol, thymol, methyl salicylate), anti-inflammatory steroidal agents (exemplified by hydrocortisone), antagonists of prostaglandin, inhibitors of prostaglandin synthetase or other key prostaglandin enzymes, antagonists of bradykinin selective for defined subtypes of bradykinin receptors, inhibitors of histamine receptors selective for receptors of subtypes which are present in human or animal dermis, or in adjacent subcutaneous tissues, or inhibitors of mast cell degranulation.

The composition may contain one or more of said agents up to a total anti-inflammatory level of from 0.01% to 10% by weight/volume.

Antibiotic

In another preferred embodiment of this invention, the vehicle combined with the local anesthetic may further include antibiotic or antifungal substances, or other similar agents well known to one skilled in prior art. These include but are not limited to bacitracin, polymyxin, nystatin. Such formulations of antibiotics are approved as Generally Safe by the United States Food and Drug Administration for "over-the counter" (subsequently referred to as OTC) sale, in that they do not require a written or verbal prescription order of a physician or other licensed practitioner. Preferably, the antibiotic is selected from the group consisting of 100–10,000 Units of bacitracin, polymyxin, and nystatin per gram of composition and from 1–10 mg. of neomycin per gram of composition.

Insect Repellent

The present embodiment may further include 1–50 or 5–15% weight/volume of an insect repellent, preferably N,N'-diethyl-m-toluamide. The combination of an insect repellent with the primary anesthetic enhances the facilitation of tick removal.

It is interesting to note that both DEET and lidocaine and the other primary anesthetics have an aromatic ring substituted by both an alkyl and an amide or an amino acyl moiety.

However, the secondary p-aminobenzoic acid anesthetics such as benzocaine, despite having a highly lipophilic character, lack such aromatic substitution as well as the ability to facilitate tick removal.

Preferred Formulations

In one preferred formulation, the primary anesthetic is selected from compounds of Formula I in which $R^1$ and $R^2=CH_3$; $R^3=H$; $R^4=CH_2$ or $CHCH_3$; $R^5=(CH_2)_nCH_3$ where $n=1–3$; and $R^6=H$ or $CH_2CH_3$.

Another preferred formulation comprises, in addition to the primary anesthetics and skin permeability enhancing carrier, at least two of an anti-inflammatory agent, an antibiotic and an insect repellent.

An especially preferred composition comprises 1–10% weight/volume of lidocaine and a water-soluble ointment or lotion carrier comprising 0.05–0.5% methyl-paraben, 0.05–0.5% propylparaben, 1–10% polyethylene glycol 2000, and 5–25% polyethylene glycol 400, 15% ethyl alcohol (wt/vol) and up to 70% esters of mixed saturated fatty acids.

A further embodiment of the invention is a method for facilitating removal of attached sucking arthropods from the skin of a mammal. This method comprises topically applying a layer of the composition described above one or more times to the sucking arthropod and the immediately surrounding topical area. One waits from 5 to 30 minutes or from 10–15 minutes after each application before re-applying the composition. After a single or the last application, one waits 5 to 30 or 10–15 minutes more, after which time the sucking arthropod either falls off or becomes easily removable using standard implements, e.g., a pair of forceps. As has been noted above, the benefit of this facilitated arthropod removal is that, unlike current removal methods, the entire arthropod is removed. No portion of the arthropod head or jaw remains in the host; consequently, the risk of infection from any remaining arthropod body portions after removal is greatly reduced using the present method.

By providing rapid and complete removal of sucking arthropods, this method preserves the arthropod for identification by skilled personnel, such as primary physicians, laboratory medical technologists, laboratory parasitologists, entomologists, or anatomic pathologists. The tests such skilled personnel may use include taxonomic identification as to the tick's species and genus, as well as determination of the presence of disease-transmitting microbiological organisms. Such analysis may include immunochemical, histochemical, or immunofluorescent examination of the removed sucking arthropod or portions of the anatomical structure of the sucking arthropod for *B. Burgdorferi* or other disease organisms which are associated with tick-borne diseases of Man or animals. Identification of disease transmitting organisms includes preparation of paraffin-imbedded sections; preparation of frozen sections; or other histological or immunological methods well known to one skilled in the area.

Still a further embodiment of the invention is a method for reducing inflammation associated with a sucking arthropod bite. In this method, one applies the composition described above one or more times to the sucking arthropod and the immediately surrounding area. The composition is one which includes at least one anti-inflammatory agent. One may apply as much of the composition to the bitten area at 7 minute intervals with the result that the discomfort arising from inflammation due to the arthropod bite is reduced and/or negatived. Since inflammation can result in swelling, reddening and pain, the present method may not only reduce discomfort from inflammation but also reduce unattractive swelling and reddening.

A further embodiment of the invention is a method for limiting infection from a sucking arthropod bite. In this method, one topically applies a thin layer of the composition including at least one antibiotic to the sucking arthropod and the immediately surrounding topical area. It is important that the first application of the composition be made within 48 hours of receiving said bite. Repeated topical applications to these areas are then made approximately every 5 to 30, preferably every 7-15 minutes until either the arthropod falls off or becomes easily removable. Since it has been found that the chances of infection from an arthropod bite are low until 48 hours after the bite, but increase dramatically thereafter, making the first application of said composition to the bite within 48 hours important. The composition not only begins to induce the arthropod jaw to relax and hence begins the process of arthropod dislocation; but further application of the composition containing antibiotic to the arthropod bite within 48 hours of that bite being made is believed to supply a sufficient amount of antibiotic to preclude infection by any disease organisms subsequently released by the arthropod. It is further desirable to apply said composition up to four or five times after removal of the arthropod to inactivate any antibiotic-sensitive disease organisms which may have been deposited by the arthropod in the host skin.

In still a further embodiment of the invention, there is provided a method of enhancing the facilitation of removing sucking arthropods by applying the composition described above including an insect repellent. Such a composition is believed to have the effect of enhancing the facilitation of removing arthropods from securing themselves in the skin. Thus in this method, one topically applies a thin layer of the composition including insert repellent to the attached sucking arthropod and the immediately surrounding topical area. Repeated topical applications to these areas are then made approximately every 5 to 30, preferably every 7-15 minutes, until either the arthropod falls off or becomes easily removable.

Another embodiment of the invention is a method of using the composition comprising the primary anesthetic a skin permeability enhancing carrier and a compound selected from the group consisting of a secondary anesthetic, an anti-inflammatory compound, an antibiotic, or an insect repellent in which said composition is applied to an area of human or animal skin bitten by a sucking arthropod, re-applying said composition to said area 7-10 minutes later if necessary and then removing said arthropod.

Another embodiment of the invention is a kit for removing sucking arthropods. The kit includes a source of the composition described above in convenient form such as a small container (e.g., a squeezable tube or sealed packet), as well as two or more supplemental items including, but not limited to an optical magnifying device; a pair of forceps; an implement for treating or bandaging the bitten dermis such as a sterile alcohol wipe pad or a sterile bandage; or a container into which the removed tick may be placed for subsequent analysis, such as a transparent plastic vial. The optical magnifying device is supplied to aid either in identifying an insect in a mammal's skin as an arthropod, or to assist in removing said arthropod after application of the composition.

EXAMPLE 1

Ticks were collected by dragging a 1 m², double thickness, white corduroy cloth attached to a 2 m lucite rod through forested vegetation adjacent to a protected reservoir area in Irvington, Westchester County, N.Y. This area is known to be heavily infested with ticks, a large percentage of which are seropositive for *Borrelia Burgdorferi*. Ticks were maintained and studied in an environmental chamber specially constructed for this purpose according to Pound et al., J. Parasitol. 75:994–996 (1989). Ticks were held at 4° C. and 97% humidity in this chamber for 1-3 months before being allowed to feed upon rabbits. Adult ticks were allowed to attach to the shaved skin of young Female New Zealand rabbits (1.5-2.5 Kg.). This was done using a plastic cup taped with surgical tape to the shaved area for a 3-hr period. At the end of this time, the plastic cup was removed and the area was examined carefully for the presence of attached ticks. See Telford et al.; Piesman et al., supra. Attached ticks and the area immediately surrounding each attached tick was treated topically with Lidocaine ointment 5.0% (w/v) (Xylocaine ®, Astra Pharmaceutical) or control (bland ointment vehicle, Schein Veterinary). The tenacity of attachment of the tick to the rabbit was noted visually. After a 2-hr period, any ticks remaining were removed manually with the aid of a fine forceps. During this procedure, the rabbits were maintained under light ketamine anesthesia. Rabbits were allowed to recover for a 2-week period as a minimum between testing procedures.

Ticks which detached in the 2-hr period after treatment with drug or control were counted.

The results of the experiment are shown in TABLE 2.

TABLE 2

| Total # of ticks attached per rabbit (N = 8) | detached with Lidocaine | detached with Control |
| --- | --- | --- |
| 15 ± 3 | 11 ± 3 | 3 ± 2 |

These results indicate a highly significant tick removal effect from the topical application of the lidocaine, as compared with bland vehicle alone. Most ticks spontaneously fell off after the Xylocaine ® ointment (lidocaine) treatment. In those few cases where removal was necessary with a curved tweezers, removal was facile and complete. On the other hand, tick removal from rabbits treated with bland ointment was difficult, even with a fine Dumont forceps, and portions of the mouthpart of the tick were sometimes left behind, which necessitated minor incision of the dermis with a #11 blade to effect complete removal.

EXAMPLE 2

Ticks were collected as in Example 1. Ticks were allowed to attach to the ears of a 35 kg, mixed-breed dog. After a 2-hr period, during which ticks attached, the animal was treated with Xylocaine ® ointment (5%, w/v) as above, or benzocaine ointment 20% (w/v). During the following 2-hr period, tick detachment was noted. Any remaining ticks were removed with aseptic procedure under Rompum ® analgesia.

The results of the experiment are shown in TABLE 3. These results indicate a highly significant effect of the topical application of the lidocaine, as compared with benzocaine ointment, in assisting the removal of the tick. In most cases, the ticks spontaneously fell off after the Xylocaine ® ointment (lidocaine) treatment. In those few cases where removal was necessary with a curved tweezers, removal was facile and complete. On the other hand, tick removal from the benzocaine-treated dog was difficult, even with a fine Dumont forceps, and portions of the mouthpart of the tick were sometimes left behind, which necessitated minor incision of the dermis with a #11 blade to effect complete removal.

TABLE 3

| Total # of Ticks Attached per trial (N = 8) | Ticks removed per trial (Lidocaine) | Ticks removed (Benzocaine) |
|---|---|---|
| 8 ± 2 | 7 ± 2 | 1 ± 1 |

EXAMPLE 3

A first group of patients was observed to have an engorged deer tick present on the dermal surface of the hand, arm, or lower leg. Lidocaine, 5.0%, w/v, in a polyethylene glycol base was applied to each patient. A second group of patients was observed to have an engorged deer tick present on the dermal surface of the hand, arm, or lower leg. Lidocaine, 5.0%, w/v, in a petroleum jelly base which was water immiscible was applied to each patient in this second group. Each application of the respective medication was repeated at 7-min intervals. This procedure was repeated for a total of thirty (30) patients. For the group of fifteen patients which received the lidocaine in the polyethylene glycol base, the tick detached in 9 of the patients after the first application, two of the patients after the second application, and two more of the patients after the third application (N=13). For the two remaining patients, the tick did not detach after the stated treatment; removal by forceps, which was facile, was required. In the second group of patients (N=15) which received the petroleum jelly-based preparation, one tick detached after the first application, one tick after the second, and two ticks after the third (N=4). For the 11 remaining patients, the tick did not detach after the stated treatment; removal by forceps, which was not facile, was required. It is therefore concluded that the petroleum jelly-based vehicle which is water-insoluble is relatively ineffective for the removal of the tick from human dermis as compared with the lidocaine contained in the polyethyleneglycol, water soluble vehicle.

EXAMPLE 4

To contrast the length of action of the anesthetic agents which might facilitate tick removal, a 5.0 mL volume of sterile lidocaine (2.0%, w/v, without epinephrine) was infiltrated using aseptic technique around the ulnar nerve of a Man, and the extent of anesthesia in the dermatome consisting of the two small digits on the hand enervated by the ulnar temporally quantified by sensitivity to a pinprick, in a manner well known to one skilled in prior art. Similarly, on another occasion in the same individual an equal volume of sterile (±)-bupivacaine (0.25%, w/v) was administered in precisely the same manner by the same practitioner. These solutions are normally used in local anesthesia for minor surgical procedures, and the two concentrations are considered to be approximately equivalent in terms of the potency of the anesthesia achieved. This study was repeated in several other normal volunteers. In the case of the (±)-bupivacaine, the mean duration of sensory analgesia in the last digit was determined to be 18±3 hours; in the case of the lidocaine it was determined to be 3±0.5 hour. Although the present invention does not involve the injection of local anesthetic, it is clear that the temporal properties of topically applied lidocaine will be shorter than those of bupivacaine. Therefore, lidocaine alone represents a preferred embodiment of the invention, when formulated in a suitable vehicle. (This discovery does not preclude the formulation of bupivacaine in combination with lidocaine, in a manner in which its longer-acting properties are less evident.) However, since the individual enantiomers of bupivacaine have widely differing serum half-lives, it is possible that a shorter-acting enantiomer could also be used.

EXAMPLE 5

Formulations of the following compositions are found to be effective, using the methodology described in Examples 1 and 2, above. It is important to note that formulations in which the local anesthetic is contained in a vehicle which does not enhance skin permeability are essentially ineffective in arthropod removal from the dermis, Thus, lidocaine at 5.0% w/v in a petroleum jelly vehicle has been found to be ineffective (see above) in contrast to the same pharmacologically active substance in a vehicle which allows enhanced dermal permeability, e.g. a vehicle having one of the formulations appearing below. Thus, the following examples are representative of formulations which will allow substantial dermal permeability of the local anesthetic. The topical formulations which follow are nonlimiting:

| | | |
|---|---|---|
| 1. | Lidocaine | 5% (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |
| 2. | Lidocaine | 5% |
| | purified water | q.s. |
| | sodium hydroxide of acetic acid- To adjust pH to 7.4 | |
| | methylparaben | 0.1% (w/v) |
| | propylparaben | 0.1% (w/v) |
| | sodium carboxymethylcellulose: adequate to adjust to a suitable consistency | |
| 3. | Lidocaine | 5% |
| | purified water | q.s. |
| | sodium hydroxide of acetic acid- To adjust pH to 7.4 | |
| | methylparaben | 0.1% (w/v) |
| | propylparaben | 0.1% (w/v) |
| | propylene glycol | 30% (w/v) |
| | polyethylene glycol 2000 | 30% (w/v) |
| | polyethylene glycol 400 | 25% (w/v) |
| | glycerol | 5% (w/v) |
| 4. | Lidocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 30% (w/v) |
| | polyethylene glycol 400 | 25% (w/v) |
| | glycerol | 5% (w/v) |
| 5. | Lidocaine | 5% (w/v) |
| | benzocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 5% (w/v) |
| | polyethylene glycol 400 | 25% (w/v) |
| | glycerol | 5% (w/v) |
| | Ethyl Alcohol | 15 % (w/v) |

-continued

| | |
|---|---|
| 6. Lidocaine | 5% (w/v) |
| dibucaine | 0.55% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 5% (w/v) |
| polyethylene glycol 400 | 25% (w/v) |
| glycerol | 5% (w/v) |
| Ethyl Alcohol | 15% (w/v) |
| 7. Bupivacaine | 0.15% (w/v) |
| Lidocaine | 5% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 5% (w/v) |
| polyethylene glycol 400 | 25% (w/v) |
| glycerol | 5% (w/v) |
| Ethyl Alcohol | 15% (w/v) |
| 8. Mepivacaine | 0.25% (w/v) |
| Lidocaine | 5% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 5% (w/v) |
| polyethylene glycol 400 | 25% (w/v) |
| glycerol | 5% (w/v) |
| Ethyl Alcohol | 15% (w/v) |
| 9. Propitocaine | 0.55% (w/v) |
| Lidocaine | 5% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 5% (w/v) |
| polyethylene glycol 400 | 25% (w/v) |
| glycerol | 5% (w/v) |
| Ethyl Alcohol | 15% (w/v) |
| 10. Lidocaine | 5% (w/v) |
| Propitocaine | 0.55% (w/v) |
| Esters of mixed, saturated fatty acids | 70% (w/v) |
| stearyl alcohol | 15% (w/v) |
| glycerin | 5% (w/v) |
| polysorbate 40 | 1% (w/v) |
| methylparaben | 0.1% (w/v) |
| propylparaben | 0.1% (w/v) |
| sodium hydroxide or acetic acid- To adjust pH to 7.4 | |
| purified water | q.s. |
| 11. Lidocaine | 5% (w/v) |
| Bupivacaine | 0.15% (w/v) |
| Esters of mixed, saturated fatty acids | 70% (w/v) |
| stearyl alcohol | 15% (w/v) |
| glycerin | 5% (w/v) |
| polysorbate 40 | 1% (w/v) |
| methylparaben | 0.1% (w/v) |
| propylparaben | 0.1% (w/v) |
| sodium hydroxide or acetic acid- To adjust pH to 7.4 | |
| purified water | q.s. |
| 12. Lidocaine | 5% (w/v) |
| Mepivacaine | 0.25% (w/v) |
| Esters of mixed, saturated fatty acids | 70% (w/v) |
| stearyl alcohol | 15% (w/v) |
| glycerin | 5% (w/v) |
| polysorbate 40 | 1% (w/v) |
| methylparaben | 0.1% (w/v) |
| propylparaben | 0.1% (w/v) |
| sodium hydroxide or acetic acid- To adjust pH to 7.4 | |
| purified water | q.s. |
| 13. Lidocaine | 5% (w/v) |
| DEET | 10% (w/v) |
| Esters of mixed, saturated fatty acids | 70% (w/v) |
| stearyl alcohol | 15% (w/v) |
| glycerin | 5% (w/v) |
| polysorbate 40 | 1% (w/v) |
| methylparaben | 0.1% (w/v) |
| propylparaben | 0.1% (w/v) |
| sodium hydroxide or acetic acid- To adjust pH to 7.4 | |
| purified water | q.s. |
| 14. Lidocaine | 5% |
| DEET | 10% (w/v) |
| purified water | q.s. |
| sodium hydroxide of acetic acid- To adjust pH to 7.4 | |
| methylparaben | 0.1% (w/v) |
| propylparaben | 0.1% (w/v) |
| sodium carboxymethylcellulose: adequate to adjust to a suitable consistency | |
| 15. Lidocaine | 5% |
| DEET | 10% (w/v) |
| purified water | q.s. |
| sodium hydroxide of acetic acid- To adjust pH to 7.4 | |
| methylparaben | 0.1% (w/v) |
| propylparaben | 0.1% (w/v) |
| propylene glycol | 30% (w/v) |
| polyethylene glycol 2000 | 30% (w/v) |
| polyethylene glycol 400 | 25% (w/v) |
| glycerol | 5% (w/v) |
| 16. Lidocaine | 5% (w/v) |
| DEET | 10% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 30% (w/v) |
| polyethylene glycol 400 | 25% (w/v) |
| glycerol | 5% (w/v) |
| 17. Lidocaine | 5% (w/v) |
| DEET | 10% (w/v) |
| benzocaine | 5% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 5% (w/v) |
| polyethylene glycol 400 | 25% (w/v) |
| glycerol | 5% (w/v) |
| Ethyl Alcohol | 15% (w/v) |
| 18. Lidocaine | 5% (w/v) |
| DEET | 10% (w/v) |
| dibucaine | 0.55% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 5% (w/v) |
| polyethylene glycol 400 | 25% (w/v) |
| glycerol | 5% (w/v) |
| Ethyl Alcohol | 15% (w/v) |
| 19. Bupivacaine | 0.15% (w/v) |
| DEET | 10% (w/v) |
| Lidocaine | 5% (w/v) |
| Polymyxin B Sulfate | 5,000 U/gm |
| bacitracin Zinc salt | 400 units/gram |
| neomycin sulfate | 5 mg/gm |
| methylparaben | 0.1% (w/v) |
| propylparaben | 0.1% (w/v) |
| propylene glycol | 30% (w/v) |
| polyethylene glycol 2000 | 5% (w/v) |
| polyethylene glycol 400 | 25% (w/v) |
| glycerol | 5% (w/v) |
| Ethyl Alcohol | 15% (w/v) |
| 20. Mepivacaine | 0.25% (w/v) |

| | | |
|---|---|---|
| | DEET | 10% (w/v) |
| | Lidocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 5% (w/v) |
| | polyethylene glycol 400 | 25% (w/v) |
| | glycerol | 5% (w/v) |
| | Ethyl Alcohol | 15% (w/v) |
| 21. | Propitocaine | 0.55% (w/v) |
| | DEET | 10% (w/v) |
| | Lidocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 5% (w/v) |
| | polyethylene glycol 400 | 25% (w/v) |
| | glycerol | 5% (w/v) |
| | Ethyl Alcohol | 15% (w/v) |
| 22. | Lidocaine | 5% (w/v) |
| | DEET | 10% (w/v) |
| | Propitocaine | 0.55% (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |
| 23. | Lidocaine | 5% (w/v) |
| | Bupivacaine | 0.15% (w/v) |
| | DEET | 10% (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |
| 24. | Lidocaine | 5% (w/v) |
| | Mepivacaine | 0.25% (w/v) |
| | DEET | 10% (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |
| 25. | (R)- or (S)- Bupivacaine | 0.5% (w/v) |
| | Lidocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 5% (w/v) |
| | polyethylene glycol 400 | 25% (w/v) |
| | glycerol | 5% (w/v) |
| | Ethyl Alcohol | 15% (w/v) |
| 26. | (R)- or (S)- Mepivacaine | 0.5% (w/v) |
| | Lidocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 5% (w/v) |
| | polyethylene glycol 400 | 25% (w/v) |
| | glycerol | 5% (w/v) |
| | Ethyl Alcohol | 15% (w/v) |
| 27. | Lidocaine | 5% (w/v) |
| | (R) or (S)- Bupivacaine | 0.5% (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |
| 28. | Lidocaine | 5% (w/v) |
| | (R) or (S)- Mepivacaine | 0.5% (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |
| 29. | (R)- or (S)- Bupivacaine | 0.5% (w/v) |
| | DEET | 10% (w/v) |
| | Lidocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 5% (w/v) |
| | polyethylene glycol 400 | 25% (w/v) |
| | glycerol | 5% (w/v) |
| | Ethyl Alcohol | 15% (w/v) |
| 30. | (R)- or (S)- Mepivacaine | 0.5% (w/v) |
| | DEET | 10% (w/v) |
| | Lidocaine | 5% (w/v) |
| | Polymyxin B Sulfate | 5,000 U/gm |
| | bacitracin Zinc salt | 400 units/gram |
| | neomycin sulfate | 5 mg/gm |
| | methylparaben | 0.1% (w/v) |
| | propylparaben | 0.1% (w/v) |
| | propylene glycol | 30% (w/v) |
| | polyethylene glycol 2000 | 5% (w/v) |
| | polyethylene glycol 400 | 25% (w/v) |
| | glycerol | 5% (w/v) |
| | Ethyl Alcohol | 15% (w/v) |
| 31. | Lidocaine | 5% (w/v) |
| | (R)- or (S)- Bupivacaine | 0.5% (w/v) |
| | DEET | 10% (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |
| 32. | Lidocaine | 5% (w/v) |
| | (R)- or (S)- Mepivacaine | 0.5% (w/v) |
| | DEET | 1 0 % (w/v) |
| | Esters of mixed, saturated fatty acids | 70% (w/v) |
| | stearyl alcohol | 15% (w/v) |
| | glycerin | 5% (w/v) |
| | polysorbate 40 | 1% (w/v) |
| | methylparaben | 0.1% (w/v) |
| | propylparaben | 0.1% (w/v) |
| | sodium hydroxide or acetic acid- To adjust pH to 7.4 | |
| | purified water | q.s. |

It is understood that the dosage of a local anesthetic, applied topically in the form of a lotion or ointment, in combination with antibiotics or other substances, as described in the present invention will be dependent upon the age, sex, health, and weight of the recipient, kind of concurrent treatment, if any, frequency of treatment, and the nature of the effect desired. The ranges of effective doses of the local anesthetics, alone or in combination formulations, as defined in the examples above are not intended to limit the inventors and represent preferred dose ranges. However, the most preferred dosage will be tailored to the individual subject, as is understood and determinable by one of skill in the art, without undue experimentation. The total dose required for each treatment may be administered by multiple doses or as a single dose. In addition to the substances declared in the above examples, a given pharmaceutical combination may contain suitable pharmaceutically acceptable carriers, such as comprising excipients and auxiliaries which facilitate processing of the active compounds into preparations which can be used pharmaceutically.

Having now fully described the invention, it will be appreciated by those of ordinary skill in the art that the same can be performed within a wide and equivalent range of formulations, procedures, and uses without affecting the spirit or scope of any aspect of the invention or any embodiment thereof.

Reference to known method steps, conventional methods steps, and known methods or conventional methods is not in any way an admission that any aspect, description, or embodiment of the present invention is disclosed, taught, or suggested in the relevant art.

The foregoing description of the specific embodiments will so fully reveal the general nature of the invention that others can, by applying knowledge within the skill of the art (including but not limited to the contents of the references cited herein), readily modify or adapt for various applications such specific embodiments, without undue experimentation, without departing from the generic concept of the present invention. Therefore, such adaptations and modifications are intended to be comprehended within the meaning and range of the disclosed embodiments, based upon the teaching and guidance which is presented herein. It is to be understood that the phraseology or terminology herein is for the purpose of description and not of limitation, such that the terminology of the present specification is to be interpreted by one normally skilled in the art in light of the teachings and guidance presented herein.

What is claimed is:

1. A method for facilitating removal of attached sucking arthropods from the skin of a mammal comprising topically applying at least one thin layer of a composition for topical application comprising
   a) 0.05–10% weight/volume of a primary anesthetic having the formula

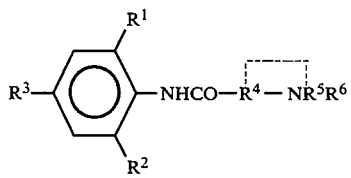

wherein
   $R^1$=H, a $C_{1-4}$ alkyl or —COOCH$_3$;
   $R^2$=H or a $C_{1-4}$ alkyl;
   $R^3$=H or CH$_3$;
   $R^4$=$C_{1-4}$ alkyl;
   $R^5$ and $R^6$ independently=H or $C_{1-4}$ alkyl,
   where at least one of $R^1$ and $R^2$ is $C_{1-4}$alkyl and where at least one of $R^5$ and $R^6$ is $C_{1-4}$ alkyl, provided that where $R^4$ and $R^5$ are joined in $R^4$—NR$^5$R$^6$, $R^4$ and $R^5$ together with N form a heterocycloalkyl moiety; or the hydrohalide thereof;
   b) a water-soluble carrier which enhances skin permeability; and
   c) a compound selected from the group consisting of
      i) 0.5–20% weight/volume of a secondary anesthetic which is a substituted ester of p-aminobenzoic acid having the formula

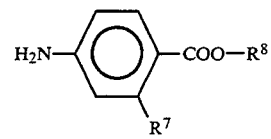

wherein $R^7$=H or Cl; $R^8$=$C_{1-4}$alkyl-X, where X=H or —N(R$^9$)$_2$, and $R^9$=$C_{1-4}$alkyl; or the hydrohalide thereof, and
      ii) 0.01–10% weight/volume of an anti-inflammatory compound,
      iii) an effective amount of an antibiotic, and
      iv) 1–50% weight/volume of an insect repellant; to the sucking arthropod and the immediately surrounding topical area, waiting 5–30 minutes from the application of said at least one thin layer and removing said sucking arthropod.

2. A method for reducing inflammation associated with a sucking arthropod bite comprising topically applying a composition comprising
   a) 0.05–10% weight/volume of a primary anesthetic having the formula

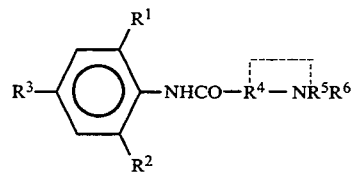

wherein
   $R^1$=H, a $C_{1-4}$ alkyl or —COOCH$_3$;
   $R^2$=H or a $C_{1-4}$ alkyl;
   $R^3$=H or CH$_3$;
   $R^4$=$C_{1-4}$ alkyl;
   $R^5$ and $R^6$ independently=H or $C_{1-4}$ alkyl,
   where at least one of $R^1$ and $R^2$ is $C_{1-4}$alkyl and where at least one of $R^5$ and $R^6$ is $C_{1-4}$alkyl, provided that where $R^4$ and $R^5$ are joined in $R^4$—NR$^5$R$^6$, $R^4$ and $R^5$ together with N form a heterocycloalkyl moiety; or the hydrohalide thereof;
   b) a water-soluble carrier which enhances skin permeability; and
   c) a compound selected from the group consisting of
      i) 0.5–20% weight/volume of a secondary anesthetic which is a substituted ester of p-aminobenzoic acid having the formula

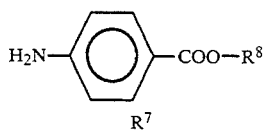

wherein $R^7$=H or Cl; $R^8$=$C_{1-4}$ alkyl-X, where X=H or —$N(R^9)_2$, and $R^9$=$C_{1-4}$alkyl; or the hydrohalide thereof, ii) 1–50% weight/volume of an insect repellent and iii) an anti-inflammatory compound selected from the group consisting of one or more of topical astringents; anti-inflammatory steroidal agents; antagonists of prostaglandin; inhibitors of prostaglandin synthetase; antagonist of bradykinin; inhibitors of histamine receptors; and inhibitors of mast cell degranulation to the sucking arthropod and the immediately surrounding topical area as is required to reduce inflammation from said arthropod bite.

3. A method of limiting infection from a sucking arthropod bite comprising topically applying a thin layer of a composition comprising:

a) 0.05–10% weight/volume of a primary anesthetic having the formula

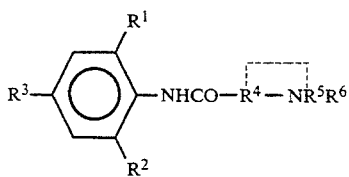

wherein $R^1$=H, a $C_{1-4}$ alkyl or —$COOCH_3$;
$R^2$=H or a $C_{1-4}$ alkyl;
$R^3$=H or $CH_3$;
$R^4$=$C_{1-4}$ alkyl;
$R^5$ and $R^6$ independently=H or $C_{1-4}$ alkyl, where at least one of $R^1$ and $R^2$ is $C_{1-4}$ alkyl and where at least one of $R^5$ and $R^6$ is $C_{1-4}$ alkyl, provided that where $R^4$ and $R^5$ are joined in $R^4$—$NR^5R^6$, $R^4$ and $R^5$ together with N form a heterocycloalkyl moiety; or the hydrohalide thereof;

b) a water-soluble carrier which enhances skin permeability; and c) a compound selected from the group consisting of i) 0.5–20% weight/volume of a secondary anesthetic which is a substituted ester of p-aminobenzoic acid having the formula

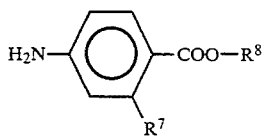

wherein $R^7$ H or Cl; $R^8$=$C_{1-4}$alkyl-X, where X=H or —$N(R^9)_2$, and $R^9$=$C_{1-4}$alkyl; or the hydrohalide thereof, and ii) 1–50% weight/volume of an insect repellent and iii) an antibiotic selected from the group consisting of one or more of from 100–10,000 unit of bacitracin, polymyxin and nystatin per gram of composition and from 1–10 mg of neomycin gram of composition; one or more times to the sucking arthropod and the immediately surrounding topical area within 48 hours of receiving said bite; making repeated topical applications of said composition in similar thin layers to said areas every 5–30 minutes until said arthropod falls off or becomes easily removable; and making up to five further applications after removal of said arthropod.

4. A method of enhancing the facilitated removal of sucking arthropods by applying a composition for topical application comprising a) 0.05–10% weight/volume of a primary anesthetic having the formula

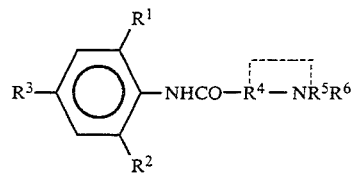

wherein $R^1$=H, a $C_{1-4}$ alkyl or —$COOCH_3$;
$R^2$=H or a $C_{1-4}$ alkyl;
$R^3$=H or $CH_3$;
$R^4$=$C_{1-4}$ alkyl;
$R^5$ and $R^6$ independently=H or $C_{1-4}$ alkyl, where at least one of $R^1$ and $R^2$ is $C_{1-4}$ alkyl and where at least one of $R^5$ and $R^6$ is $C_{1-4}$ alkyl, provided that where $R^4$ and $R^5$ are joined in $R^4$—$NR^5R^6$, $R^4$ and $R^5$ together with N form a heterocycloalkyl moiety; or the hydrohalide thereof;

b) a water-soluble carrier which enhances skin permeability; and c) a compound selected from the group consisting of 0.5–20% weight/volume of a secondary anesthetic which is a substituted ester of p-aminobenzoic acid having the formula

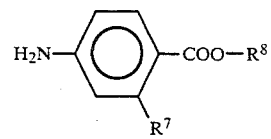

wherein $R^7$=H or Cl; $R^8$=$C_{1-4}$alkyl-X, where X=H or —$N(R^9)_2$, and $R^9$=$C_{1-4}$alkyl; or the hydrohalide thereof, and ii) 0.01–10% weight/volume of an anti-inflammatory compound, iii) an effective amount of an antibiotic, and iv) 1–50% weight/volume of N,N'-diethyl-m-tolua-mide; to the sucking arthropod and the immediately surrounding topical area.

5. A method of using a composition for topical application of arthropod removal comprising a) 0.05–10% weight/volume of a primary anesthetic having the formula

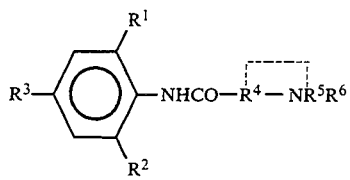

wherein
- $R^1$ = H, a $C_{1-4}$ alkyl or —COOCH$_3$;
- $R^2$ = H or a $C_{1-4}$ alkyl;
- $R^3$ = H or CH$_3$;
- $R^4$ = $C_{1-4}$ alkyl;
- $R^5$ and $R^6$ independently = H or $C_{1-4}$ alkyl, where at least one of $R^1$ and $R^2$ is $C_{1-4}$alkyl and where at least one of $R^5$ and $R^6$ is $C_{1-4}$ alkyl, provided that where $R^4$ and $R^5$ are joined in $R^4$—$NR^5R^6$, $R^4$ and $R^5$ together with N form a heterocycloalkyl moiety; or the hydrohalide thereof;
- b) a water-soluble carrier which enhances skin permeability; and
- c) a compound selected from the group consisting of i) 0.5–20% weight/volume of a secondary anesthetic which is a substituted ester of p-aminobenzoic acid having the formula

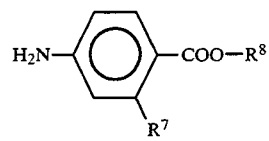

wherein $R^7$ = H or Cl; $R^8$ = $C_{1-4}$alkyl-X, where X = H or —N($R^9$)$_2$, and $R^9$ = $C_{1-4}$alkyl; or the hydrohalide thereof, and ii) 0.01–10% weight/volume of an anti-inflammatory compound, iii) an effective amount of an antibiotic, and iv) 1–50% weight/volume of an insect repellent said method comprising applying said composition to a sucking arthropod attached to human or animal skin and the immediately surrounding topical area, re-applying said composition to said area 7–10 minutes later and then removing said arthropod.

* * * * *